US010299697B2

(12) United States Patent
Cho et al.

(10) Patent No.: US 10,299,697 B2
(45) Date of Patent: May 28, 2019

(54) MICROELECTRODE FOR MEASURING EMG OF LABORATORY MICROFAUNA AND METHOD FOR MANUFACTURING THE SAME, AND SYSTEM FOR MEASURING EMG OF LABORATORY MICROFAUNA USING MICROELECTRODE

(71) Applicants: GWANGJU INSTITUTE OF SCIENCE AND TECHNOLOGY, Gwangju (KR); CHONNAM NATIONAL UNIVERSITY HOSPITAL, Gwangju (KR); DAEGU GYEONGBUK INSTITUTE OF SCIENCE & TECHNOLOGY, Daegu (KR)

(72) Inventors: Sung-Joon Cho, Gwangju (KR); Seok-Yong Choi, Gwangju (KR); Tai-Seung Nam, Gwangju (KR); Dong-Hak Byun, Gwangju (KR); So-Hee Kim, Gwangju (KR); Myeong-Kyu Kim, Gwangju (KR)

(73) Assignees: GWANGJU INSTITUTE OF SCIENCE AND TECHNOLOGY, Gwangju (KR); CHONNAM NATIONAL UNIVERSITY HOSPITAL, Gwangju (KR); DAEGU GYEONGBUK INSTITUTE OF SCIENCE & TECHNOLOGY, Daegu (KR)

( * ) Notice: Subject to any disclaimer, the term of this patent is extended or adjusted under 35 U.S.C. 154(b) by 662 days.

(21) Appl. No.: 14/931,758

(22) Filed: Nov. 3, 2015

(65) Prior Publication Data

US 2016/0178604 A1 Jun. 23, 2016

(30) Foreign Application Priority Data

Nov. 3, 2014 (KR) .......................... 10-2014-0151383

(51) Int. Cl.
*A61B 5/0492* (2006.01)
*G01N 33/483* (2006.01)
*A61B 5/04* (2006.01)

(52) U.S. Cl.
CPC ....... *A61B 5/0492* (2013.01); *G01N 33/4833* (2013.01); *A61B 5/04001* (2013.01); *G01N 33/4836* (2013.01)

(58) Field of Classification Search
CPC .......................... A61B 5/0492; A61B 5/04001; A61B 5/1495; G01N 33/4836; G01N 33/483

(Continued)

(56) References Cited

U.S. PATENT DOCUMENTS 5,215,088 A * 6/1993 Normann ........... A61B 5/04001
600/377
2004/0006264 A1 * 1/2004 Mojarradi ............ A61B 5/0478
600/378

(Continued)

OTHER PUBLICATIONS

Sohee Kim et. al., Development of flexible penetrating neural microelectrodes, Core Research Project Final Report by Ministry of Science with the English summary on p. 5, May 21, 2014, May 2014, ICT & Future Planning, Republic of Korea.

(Continued)

*Primary Examiner* — Lee S Cohen
*Assistant Examiner* — Sean W Collins
(74) *Attorney, Agent, or Firm* — Hauptman Ham, LLP

(57) ABSTRACT

The present disclosure relates to a microelectrode for measuring EMG signals of a laboratory microfauna. The present disclosure includes a metal plate with an insulating plate deposited on a surface, a plurality of silicon substrates disposed on the insulating plate, the silicon substrates being electrically connected to the metal plate, covered with an insulator, and adjacent to one another, and a plurality of needle electrodes, each formed on the respective silicon (Continued)

substrates as an integral part thereof, wherein the needle electrodes have the same predetermined length, have a tapered shape from the respective silicon substrates, are spaced apart from each other by a predetermined distance, and wherein a metallic layer is formed on each of the needle electrodes by depositing metal materials, the insulator is formed on the metallic layer, and a portion of the metallic layer at a tip is exposed.

6 Claims, 11 Drawing Sheets

(58) Field of Classification Search
USPC .......................................... 600/373, 378, 393
See application file for complete search history.

(56) References Cited

U.S. PATENT DOCUMENTS

| 2009/0030298 A1* | 1/2009 | Matthews | A61B 5/04 600/383 |
| 2009/0247898 A1* | 10/2009 | Robitzki | G01N 27/041 600/547 |
| 2010/0268055 A1* | 10/2010 | Jung | A61B 5/04001 600/377 |
| 2011/0028822 A1* | 2/2011 | Beck | A61B 5/0408 600/386 |
| 2015/0208984 A1* | 7/2015 | Huang | A61B 5/685 600/393 |

OTHER PUBLICATIONS

Korean Office Action dated Jan. 28, 2016 in connection with the counterpart Korean Patent Application No. 10-2014-0151383, citing the above reference(s).

* cited by examiner

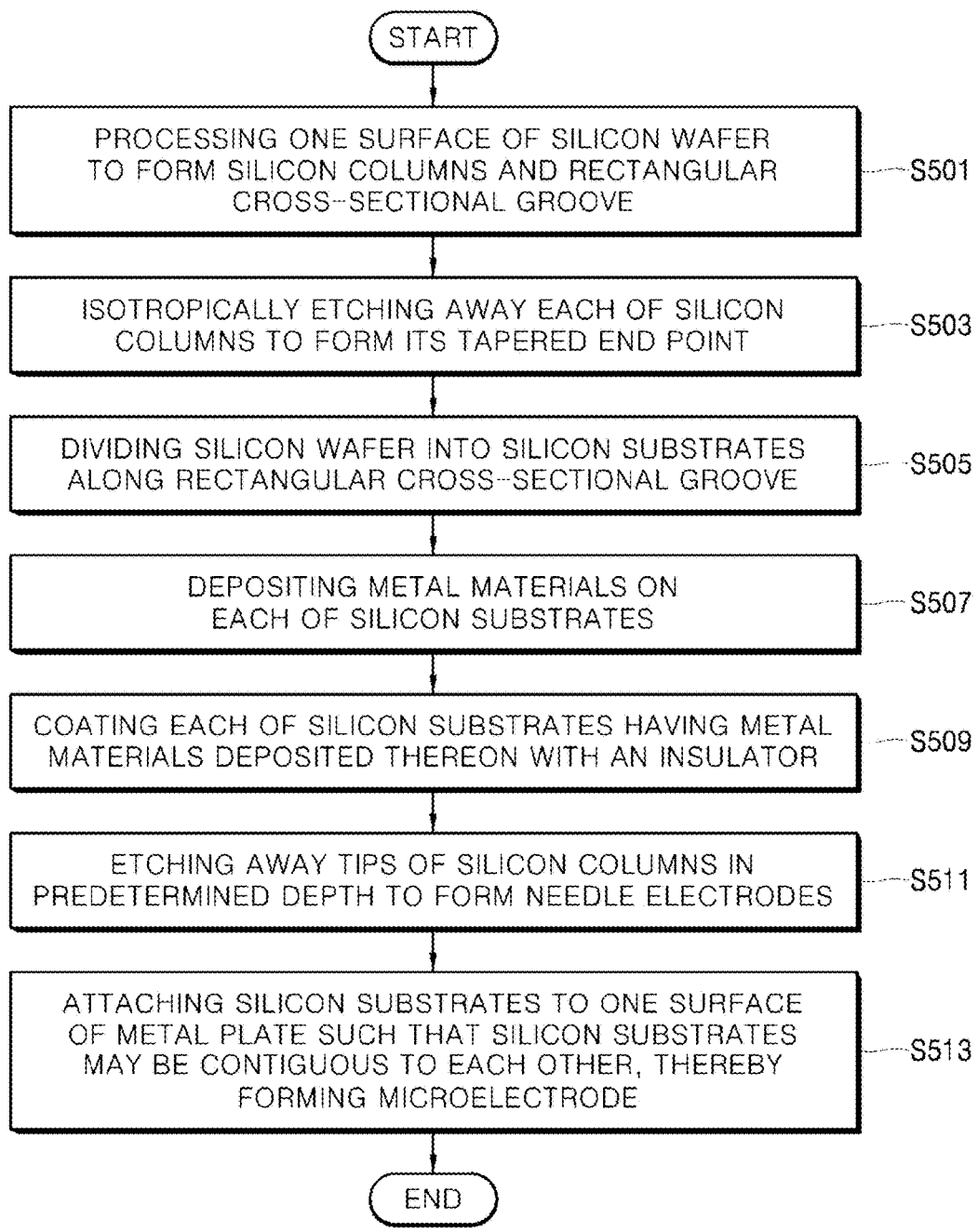

MICROELECTRODE FOR MEASURING EMG OF LABORATORY MICROFAUNA AND METHOD FOR MANUFACTURING THE SAME, AND SYSTEM FOR MEASURING EMG OF LABORATORY MICROFAUNA USING MICROELECTRODE

CROSS-REFERENCE TO RELATED APPLICATIONS

This application claims the priority of Korean Patent Application No. KR 10-2014-0151383 filed on Nov. 3, 2014, in the Korean Intellectual Property Office, the disclosure of which is incorporated herein by reference.

BACKGROUND

1. Technical Field

The present disclosure relates to a microelectrode, and in particular, a microelectrode for measuring electromyographic (EMG) signals of laboratory microfauna, a method for manufacturing the microelectrode, and a system for measuring the EMG signals of the laboratory microfauna.

2. Description of the Related Art

An electromyography refers to a test for recording electrical activity produced when muscle fibers are contracted and thereby evaluating a function of a muscle. The electromyography is generally classified into an electroneuromyography and a needle electromyography.

In particular, the needle electromyography is a test for using a needle electrode to monitor an abnormal electrophysiological change coming out of a muscle when a nerve is injured or if the muscle itself is abnormal and diagnose whether the muscle is normal or abnormal.

The electromyography may facilitate the observation on a variety of diseases including a fibrillation potential, a positive sharp wave, a fascicular contraction potential, a myokymia discharge, a complex continuous discharge and so on. Such abnormal spontaneous activity may be a serious disease to disrupt one's daily life. The electromyography has employed a needle electrode.

The needle electrode has a size small enough to collect electric signals coming out from one nerve fiber. The needle electrode may allow one to identify which phenomenon happens when electricity flows within a cell or a nerve.

In general, needle electrodes for measuring EMG use a monopolar electrode and a bipolar electrode of ambipolarity.

The monopolar electrode has problems that it is not stiff enough to be used in a deep muscle, has unstable electric signals, and is uneconomical because it can be used only one time in spite of a high-cost.

The bipolar electrode has two polarities in a single needle electrode and has problems that it has a significantly narrow measuring range and gives pains and unpleasant feelings to a subject.

As mentioned above, such conventional needle electrodes have disadvantages that they give pains and unpleasant feelings to a subject as well as cannot be reused in spite of a high-cost. Therefore, what is needed is replacement of the conventional needle electrodes. Korean Patent Laid-open Publication No. 2011-0106234 discloses an electrode for measuring physiological signals from a skin when the electrode is adhered to the skin, in which the physiological signals are measured using a plurality of needles formed on a side of contact part in a size penetrable through a stratum corneum of the skin. However, objects and configurations of the above Korean Patent Laid-open Publication No. 2011-0106234 differ from those of the present disclosure that EMG signals are measured from microfauna whose gene information is analogue to a human being.

SUMMARY

An object of the present disclosure is to provide a microelectrode for measuring EMG signals from microfauna whose gene information is analogue to a human being in order to develop a therapy for curing a disease such as a muscle anomaly.

Another object of the present disclosure is to provide a method for manufacturing the microelectrode used to measure the EMG signals from the microfauna.

Yet another object of the present disclosure is to provide system using the microelectrode to measure the EMG signals from the microfauna.

In accordance with one aspect of the present invention, provided is a microelectrode for measuring EMG signals of a laboratory microfauna, comprising: a metal plate with an insulating plate deposited on a surface; a plurality of silicon substrates disposed on the insulating plate, the silicon substrates being electrically connected to the metal plate, covered with an insulator, and adjacent to one another; and a plurality of needle electrodes, each formed on the respective silicon substrates as an integral part thereof, wherein the needle electrodes have the same predetermined length, have a tapered shape from the respective silicon substrates, are spaced apart from each other by a predetermined distance, and wherein a metallic layer is formed on each of the needle electrodes by depositing metal materials, the insulator is formed on the metallic layer, and a portion of the metallic layer at a tip is exposed.

The needle electrodes are inserted to the microfauna together to collect bio-signals of the microfauna using the exposed parts of the metallic layers at the tips.

The metallic layer is covered with the insulator by performing a chemical vapor deposition (CVD) in each of the needle electrodes, and the metallic layer is exposed by etching away the tip by performing a Reactive Ion Etching (RIE) in each of the needle electrodes.

The metallic layer consists of chrome (Cr), gold (Au), and iridium (Ir), the iridium being thicker than the chrome and the gold.

The metallic layer is formed by depositing the metallic materials in the silicon substrates and the silicon substrates are coupled with the metal plate by wires to deliver bio-signals measured from the microfauna to the metal plate.

The silicon substrates are formed as a single piece and then separated from each other, and are disposed adjacent to each other on the insulating plate.

The bio-signals are produced from zebrafish, vertebrate, whose gene information is analogous to a human being.

In accordance with one aspect of the present invention, provided is a method for manufacturing a microelectrode used to measure EMG signals of microfauna, comprising: processing one surface of a silicon wafer to form a plurality of silicon columns and a rectangular cross-sectional groove; isotropically etching away each of the silicon columns to form a sharp distal end; dividing the silicon wafer into a plurality of silicon substrates along the rectangular cross-sectional groove; depositing metal materials on the silicon substrates, respectively; coating each of the silicon substrates having the metal materials deposited thereon with an insulator; etching away tips of the silicon columns in a predetermined depth to form a plurality of needle electrodes;

and attaching the silicon substrates to one surface of a metal plate such that the silicon substrates are adjacent to each other, thereby forming the microelectrode.

The forming a plurality of needle electrodes includes: dipping the plurality of silicon substrates having the plurality of silicon columns in a silicon well such that the tips come out of the silicon well; masking other portion of the silicon columns than the tips; and etching away the coming out tips of the silicon columns by a Reactive Ion Etching (RIE), thereby forming the needle electrodes.

The depositing metallic materials includes depositing chrome (Cr) and gold (Au) of metallic materials on the silicon substrates; and depositing the iridium (Ir) thicker than the chrome and the gold on the silicon substrates.

The forming the microelectrode further includes: connecting the metal plate to the silicon substrates by soldering wires such that the needle electrodes are electrically connected to an external device.

In accordance with yet another aspect of the present invention, provided is a system for measuring bio-signals from laboratory microfauna using the microelectrode of claims 1 to 11, comprising: a position control unit, attaching the microelectrode, for controlling the position of the microelectrode; a microfauna mounting unit for mounting the microfauna; a microfauna mounting unit, disposed at an opposite direction to the position control unit, for dipping the microfauna; and a magnification unit for magnifying the microelectrode and the microfauna in order to control the position control unit and the microfauna mounting unit, contact the microelectrode to the microfauna, and measure bio-signals from the microfauna.

The position control unit includes a magnet section disposed at one side of the microelectrode to fix the microelectrode.

The position control unit is supplied a power from an external device to apply the power into needle electrode included in the microelectrode in order to measure bio-signals from the microfauna, thereby causing the needle electrode inserted into the microfauna to produce stimulus signals.

The microfauna mounting unit includes a ground electrode such that the microfauna containing the microelectrode can be applied stimulus signals output from the microelectrode to produce bio-signals.

The microfauna mounting unit may be rotated such that the microelectrode may be accurately inserted into the microfauna.

The microfauna mounting unit puts thereon the agarose block containing the microfauna therein.

The microfauna mounting unit has a coil electrode having a shape of winding around the microfauna The coil electrode is composed of an electric conductive material and both ends thereof are grounded.

The bio-signals are produced from zebrafish, vertebrate, whose gene information is analogous to a human being.

Therefore, according to the present disclosure, it is possible to measure EMG signals using microfauna not a human being, thereby developing a therapy for curing against problems such as a muscle anomaly.

According to the present disclosure, it is possible to insert two microelectrodes at once, thereby observing a range wider than a monopolar electrode and more accurately measuring the EMG signals than a bipolar electrode.

According to the present disclosure, it is possible to use a novel coil electrode, thereby innovatively enhancing a signal-to-noise ratio.

According to the present disclosure, it is more economical than conventional electrodes because it can be manufactured at a low cost and further reused.

However, the effects and advantages of the present disclosure are not limited to the foregoing and other effects and advantages will be clearly understood to those skilled in the art from what is described below.

BRIEF DESCRIPTION OF DRAWINGS

FIG. 3 is a flowchart illustrating a method for manufacturing the microelectrode used to measure the EMG signals from the laboratory microfauna according to one embodiment of the present disclosure;

DETAILED DESCRIPTION

Figure 1:
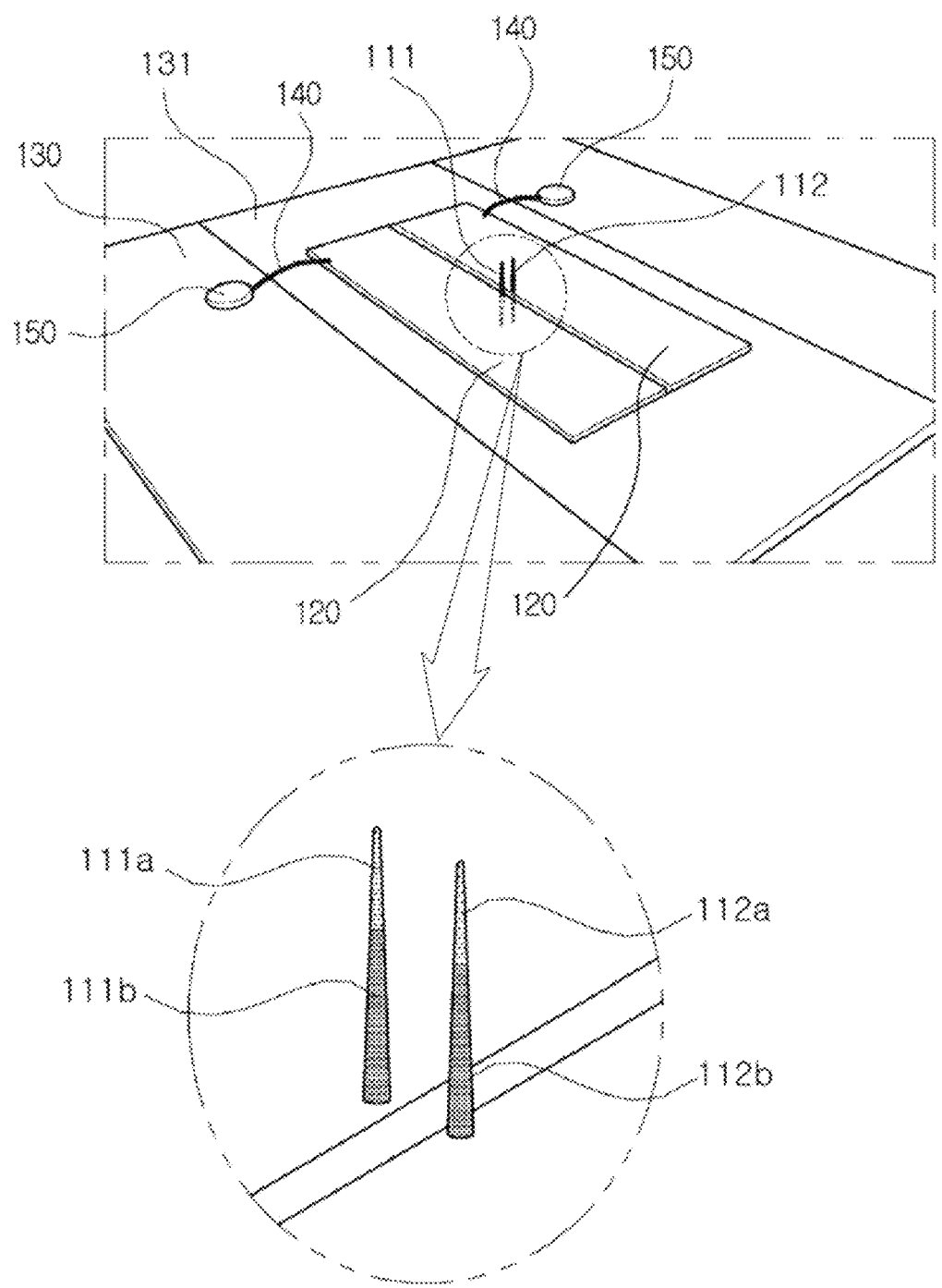
FIG. 1 is block diagrams illustrating a microelectrode for measuring EMG signals from laboratory microfauna according to one embodiment of the present disclosure.

In order to fully understand the present disclosure, operational advantages of the present disclosure, and objects achieved by the practice of the present disclosure, the accompanying drawings and the descriptions thereof illustrating preferred embodiments of the present disclosure should be referenced.

While embodiments of the present disclosure will be described in detail with reference to the accompanying drawings hereinafter, the present disclosure may be implemented in a variety of forms and not limited to such embodiments. Parts irrelevant to the present disclosure are omitted to avoid obscuring aspects of the present disclosure, and like reference numerals refer to like parts throughout the various figures.

It is to be noticed that the term □comprising□, used in the present description and claims, should not be interpreted as being restricted to the means listed thereafter; it does not exclude other elements or steps unless stated otherwise.

Further, the terms □ . . . unit□, □ . . . section□, □module□, □block□ and so on as used herein refer to a base unit by which one function or operation is processed, which may be implemented in hardware, software, or a combination of hardware and software.

FIG. 1 is block diagrams illustrating a microelectrode for measuring EMG signals of laboratory microfauna according to an embodiment of the present disclosure.

Referring to FIG. 1, the microelectrode 100 for measuring the EMG signals of the laboratory microfauna includes needle electrodes 110, silicon substrates 120 and a metal plate 130.

The needle electrodes 110 are formed in a taper shape to respective end points, i.e., a needle shape. The needle electrodes 110 can measure fine bio-signals spontaneously produced in the microfauna. Herein, a zebrafish, a kind of vertebrates, is used whose gene information and an organ system are analogous to a human being, as the microfauna.

Further, the needle electrodes 110 may include an active electrode 111 for measuring spontaneous bio-signals of the microfauna and a reference electrode 112 acting as a ground. The active electrode 111 may stimulate the microfauna by applying a power supplied from an external device to the microfauna and obtain microfauna's bio-signals produced by the stimulation.

Each of the needle electrodes 110 may be formed on the respective silicon substrates 120 as an integral part. The needle electrodes 110 are made of a silicon material because such a silicon material has a good durability and may be easily reused. Each of the needle electrodes 110 may be formed to have a diameter of 75 μm at its bottom attached to the corresponding silicon substrate 120. Further, the needle electrodes 110 may have the same predetermined length, e.g., 1300 μm, such that they can be sufficiently inserted into the microfauna.

To be inserted into the microfauna, each of the needle electrodes 110 may have a tapered shape i.e., a needle shape, away from the respective silicon substrates in the vertical direction.

Such a needle shape of the needle electrodes 110 may be achieved through a dicing and an isotropic etching. The dicing is to process a silicon wafer in a shape of a dice. The etching is to go through a chemical treatment so as to remove unnecessary portions other than preferred portions. The etching, which is well known in the art to be used for a silicon wafer processing, includes a dry etching and a wet etching. The needle electrodes 110 used in the present disclosure are formed through the wet etching but not limited thereto and may be formed according to any known conventional techniques.

The needle electrodes 110 are spaced apart from each other by a predetermined distance, e.g., 700 μm or less, to stably collect bio-signals without signal interference.

Figure 2:
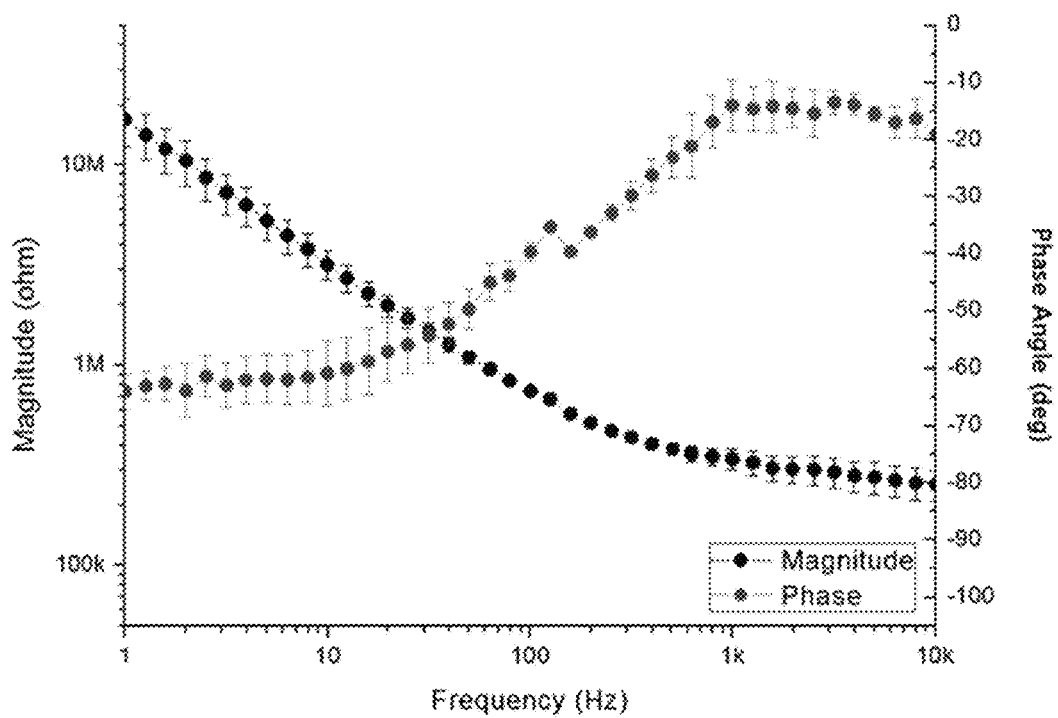
FIG. 2 is a graph illustrating impedances and phases of iridium (Ir) in metallic materials according to one embodiment of the present disclosure.
Figure 4A:
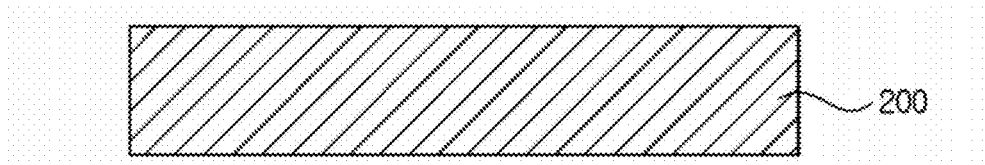
FIG. 4 is block diagrams illustrating a process for manufacturing the microelectrode used to measure the EMG signals from the laboratory microfauna according to another embodiment of the present disclosure.
Figure 4B:
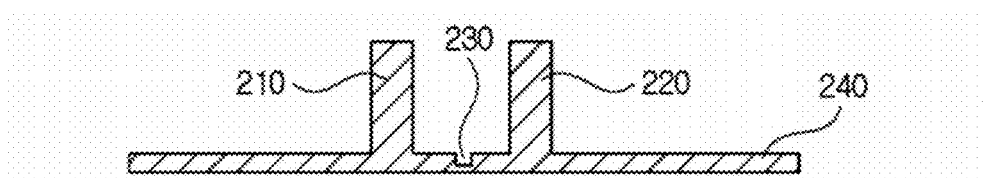
Figure 4C:
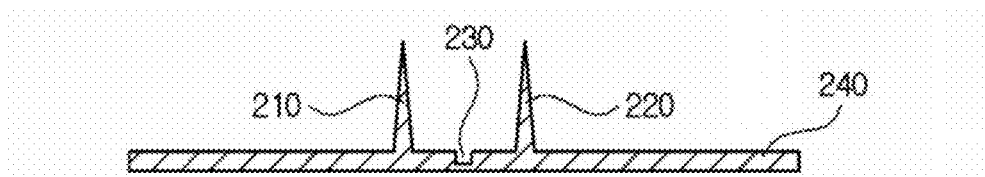
Figure 4D:
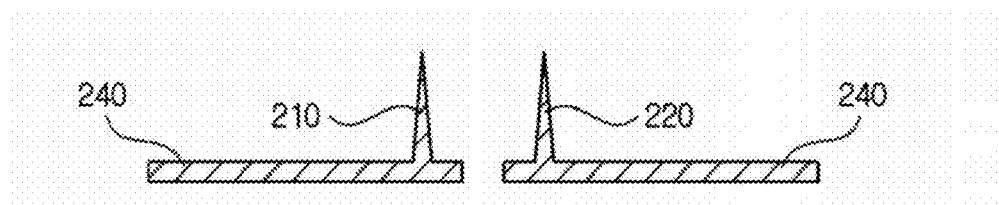
Figure 4E:
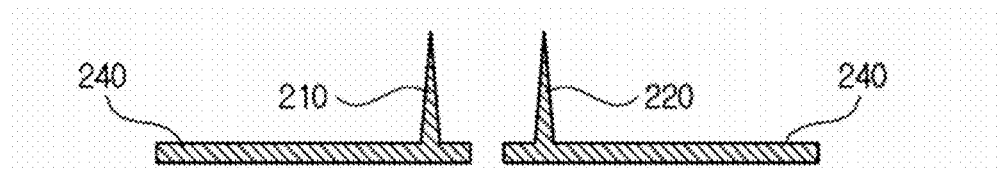
Figure 4F:
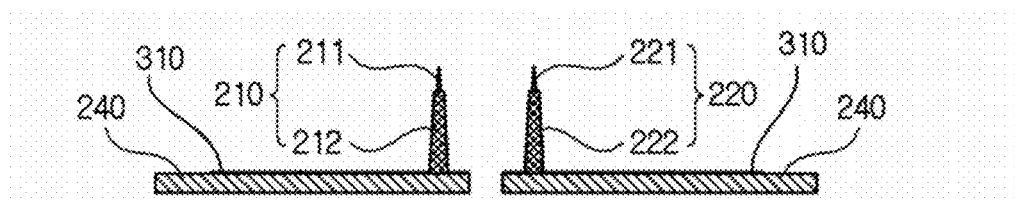
Figure 4G:
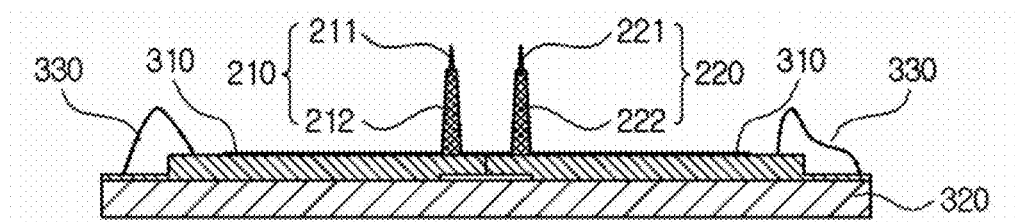

Each of the needle electrodes 110 may include a metallic layer formed by depositing metal materials, through which a power is supplied and bio-signals can be collected. The metal materials used herein may include chrome (Cr), gold (Au) and iridium (Ir). For example, Cr and Au are deposited on each of the needle electrodes 110 in a thickness of 100 nm and then Ir is deposited thereon in a thickness of 500 nm, and as a result, each of the needle electrodes 110 may have the metallic layer formed on its peripheral surface. Such thicknesses of the metal materials are resultant values which are gained by experiments and may provide preferable electric characteristics to the needle electrodes 110. Referring to FIG. 2, Ir exhibits stable electric characteristics over the whole frequency range and thus may be used as a major element constituting the metallic layer.

To preserve the electric characteristics, each of the needle electrodes 110 includes an insulator formed on the metallic layer. The insulator is coated on the metallic layer by a Chemical Vapor Deposition (CVD). The CVD according to the present disclosure may be used for the coating of the insulator, which may be specifically a parylene coating. The parylene coating refers to a polymer coating deposited on a subject (the microelectrode of the present disclosure) on a micrometer thickness basis in a gaseous state irrespective of its shape at room temperature in vacuum. A film generated by the parylene coating is amorphous and linear and exhibits a superior hydrophobic property, and thus does not effectuate an explosive chemical reaction. The parylene used as the insulator used herein is a parylene C, which exhibits superior electric insulation, mechanical strength and physical property, acts as an excellent moisture and corrosive gas barrier, and has an outstanding chemical resistance, and therefore, may be used as insulators for the needle electrodes 110.

To collect the bio-signals of the microfauna, each of the needle electrodes 110 may be formed such that portions of the metallic layers, i.e., tips 111a and 112a, of the needle electrodes 110 are exposed. The bio-signals sought to collect from the microfauna are electromyographic (EMG) signals. The EMG signals are to indicate an electrical change in muscular reactions to neural stimuli. The microelectrode according to the present disclosure collects the electromyographic signals used to develop a therapy for curing muscle diseases of a human being from the microfauna.

Specifically, after the insulators are coated, the tips 111a and 121a of the needle electrodes 110 are etched away by a predetermined depth according to a predetermined method, and as a result, the portions of the metallic layers of the needle electrodes 110 can be exposed. The method for etching away the tips 111a and 112a may be a Reactive Ion Etching (RIE) in which the portions of insulators formed in the tips 111a and 112a of the needle electrodes 110 may be removed using O₂ plasma.

Lengths of the tips 111a and 112a of the needle electrodes 110 influence on the electric characteristics. As such an influence on the electric characteristics, under-exposed metallic layers of the needle electrodes 110 may result in a high impedance requiring a high voltage. This means that overly small areas of the exposed metallic layers of the needle electrodes 110 cannot detect the fine signals of the microfauna.

Accordingly, each of the needle electrodes 110 needs to have a properly exposed metallic layer to collect the bio-signals of the microfauna when the needle electrodes 111 are inserted into the microfauna. On the contrary, over-exposed metallic layers of the needle electrodes 110 may be more sensitive to noises and reduce options in measuring the bio-signals. Therefore, the lengths of the tips 111a and 112a of the needle electrodes 110 may be set to be neither too long nor too short, e.g., 100 μm.

Each of the silicon substrates 120 is integrated with the respective needle electrodes 110 as an integral part such that it has one of the needle electrodes 110 on one surface thereof. The silicon substrates 120 are adjacent to each other on an insulating plate 131 deposited on the metal plate 130. Further, each of the silicon substrates 120 have a metallic layer formed thereon and may be connected to the metal plate 130 by wires to be supplied a power from the metal plate 130, as in the needle electrodes 110. Metallic layers formed on the silicon substrates 120 are formed in the same way as those formed on the needle electrodes 110.

The silicon substrates 120 may apply the supplied power to the needle electrodes 110. Each of the silicon substrates 120 may be covered with an insulator on its peripheral region for the stable electric characteristics of the needle electrodes 110. The insulators of the silicon substrates 120 are formed in the same way as the insulators formed on the needle electrodes 110. When covered with the insulators, peripheral regions of the silicon substrates 120 are masked with a tape, e.g., a sticky tape, to prevent the metallic layers in the peripheral regions from being covered with the insulators, and thus may be electrically coupled with the metal plate 130 by the wires.

The metal plate 130 has the insulating plate 131 formed on its one surface thereof for the stable electric characteristics for the needle electrode 130 and may be disposed on the other sides of the silicon substrates 120 attaching to the insulting plate 131. Further, the metal plate 130 may be electrically coupled with the silicon substrates 120 by the wires 140. The metal plate 130 is coupled with the wires 140 through, for example, a soldering, and therethrough, solders 150 may be made at points where the metal plate 140 encounters the wires 140. Hence, the metal plate 130 may be supplied the power from an external device to apply the power into the needle electrodes 110 through the silicon substrates 120. The metal plate 130 may be formed from a copper exhibiting a superior electric conductivity but is not limited thereto.

The microelectrode may observe a wider range than a conventional bipolar electrode and accurately detect signals since the needle electrodes 110 are inserted into the microfauna together.

Figure 5:
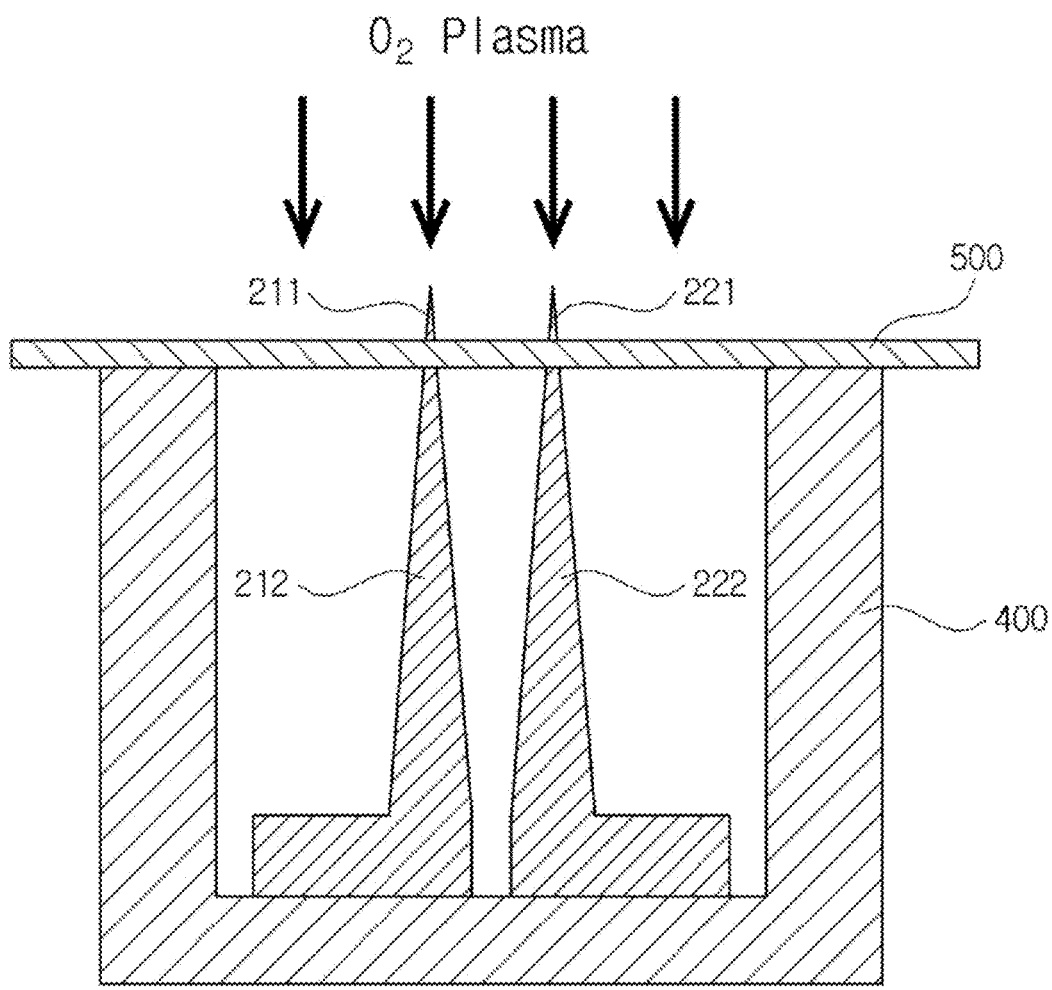
FIG. 5 is a block diagram illustrating a process for forming the microelectrode using a Reactive Ion Etching (RIE) scheme according to yet another embodiment of the present disclosure.
Figure 6:
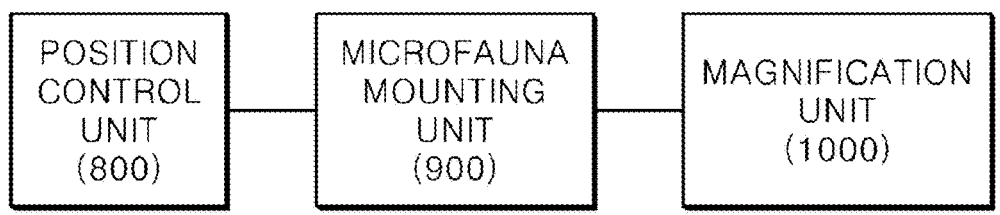
FIG. 6 is a schematic block diagram illustrating a system using the microelectrode to measure the EMG signals from the laboratory microfauna according to yet still another embodiment of the present disclosure.

FIG. 5 is a flowchart illustrating a method for manufacturing the microelectrode for measuring the EMG signals of the laboratory microfauna according to another embodiment of the present disclosure and FIG. 6 is block diagrams illustrating a process for manufacturing the microelectrode for measuring the EMG signals of the laboratory microfauna according to another embodiment of the present disclosure.

Referring to FIG. 5, the method for manufacturing the microelectrode for measuring the EMG signals of the laboratory microfauna according to another embodiment of the present disclosure may include processing one surface of a silicon wafer to form a plurality of silicon columns and a rectangular cross-sectional groove (S501), isotropically etching away each of the silicon columns to form its tapered end point (S503), dividing the silicon wafer into a plurality of silicon substrates along the rectangular cross-sectional groove (S505), depositing metal materials on each of the silicon substrates (S507), coating each of the silicon substrates having the metal materials deposited thereon with an insulator (S509), etching away tips of the silicon columns in a predetermined depth to form a plurality of needle electrodes (S511), and attaching the silicon substrates to surface of a metal plate such that the silicon substrates may be adjacent to each other, thereby forming the microelectrode (S513).

Hereinafter, the process for manufacturing the microelectrode for measuring the EMG signals of the laboratory microfauna according to another embodiment of the present disclosure will be described.

Referring to FIG. 6, in steps (a) and (b), a silicon wafer 200 is prepared and then silicon columns 210 and 220 are formed by a predetermined method. The silicon wafer 200 is employed because it has a good durability can be easily reused. The method for forming the silicon columns is a dicing. For example, the silicon columns 210 and 220 are formed by vertically cutting out the silicon wafer 200 of a thickness of 2 mm by a depth of 1700 μm. A distance between the silicon columns 210 and 220 is 500 μm. Further, formed between the silicon columns 210 and 220 is a rectangular cross-sectional groove 230. The rectangular cross-sectional groove 230 may be configured to be in a depth of 50 μm and a width of 200 μm.

In step (c), the silicon columns 210 and 220 are isotropically etched away in a shape that their end points are tapered. The etching used herein is a wet etching in which processes a cuboid shape of the silicon columns into a cone shape using an etchant solution such that their end points are tapered, where the etchant solution is composed of HF of 48% ionization to $HNO_3$ of 59% ionization in a ratio of 1:19, for example. Describing the wet etching process in detail, the silicon columns are rotated by an overhead stirrer and at the same time immersed into the etchant solution, as described above, stirred by a magnetic stirrer for three minutes. The magnetic stirrer spins at 20 rpm and the overhead stirrer spins at 500 rpm in a counter direction to the magnetic stirrer.

Then, the silicon columns remain immersed for five minutes without being rotated nor stirred. The overhead stirrer rotates the silicon columns in a chemical solution by a customization designed Teflon. The silicon columns get rounded peripheral surfaces and tapered end points by going though such two procedures.

In step (d), the silicon wafer 200 is divided into a plurality of silicon substrates 240 along the rectangular cross-sectional groove in preparation for deposition of metal materials and coating of insulators following the step (d). At this case, the division of the silicon wafer 300 is done by a physical force.

In step (e), the metal materials are deposited on the silicon wafer 200. That is, the metal materials are deposited on the silicon columns 210 and 220 and the silicon substrates 240. The metal materials used herein may be chrome (Cr), gold (Au) and iridium (Ir).

The Cr and Au are deposited in a thickness of 100 nm and the Ir in a thickness of 500 nm, and as a result, the metallic layers are formed over the silicon columns 210 and 220 and the silicon substrates 240. The present disclosure employs the CVD although such a deposition may be done by any of known methods.

In step (f), each of the silicon columns 210 and 220 is coated with an insulator. The insulator is a parylene C and is coated on the silicon columns 210 and 220 according to the CVD. Prior to the coating of the parylene C, peripheral regions of the silicon substrates 240 are masked with tapes (e.g., sticky tapes). The masked peripheral regions of the silicon substrates 240 may be coupled with an external device (e.g., an EMG measuring device). Unmasked regions 310 of silicon substrates 240 are insulated by the insulators, thereby protecting the electric characteristics of the microelectrode.

In step (f), tips 211 and 221 of the silicon columns 210 and 220 are etched away in a predetermined depth, and whereby a plurality of needle electrodes is formed. The tips 211 and 221 whose insulators are removed by the etching may enable the EMG signals of the microfauna to be collected. The method for removing the insulators may be a RIE as described below in detail.

Finally, in step (g), the silicon substrates 240 divided from the silicon wafer 200 are attached to one surface of a metal plate 320 such that the silicon substrates may be adjacent to each other, thereby forming the microelectrode. Specifically, the metal plate 320 has an insulating plate formed on one surface thereof for stabilizing the electric characteristics of the microelectrode, and the silicon substrates 240 are attached to the insulating plate formed on the metal plate 320. Further, the silicon substrates 240 may be electrically coupled with the metal plate 320 by wires 330 to deliver measured bio-signals to an outside. The wires 330 may be attached to the metal plate 320 and the silicon substrates 240 through soldering. The metal plate 320 may be from a copper which exhibits a superior electric conductivity.

Figure 7:
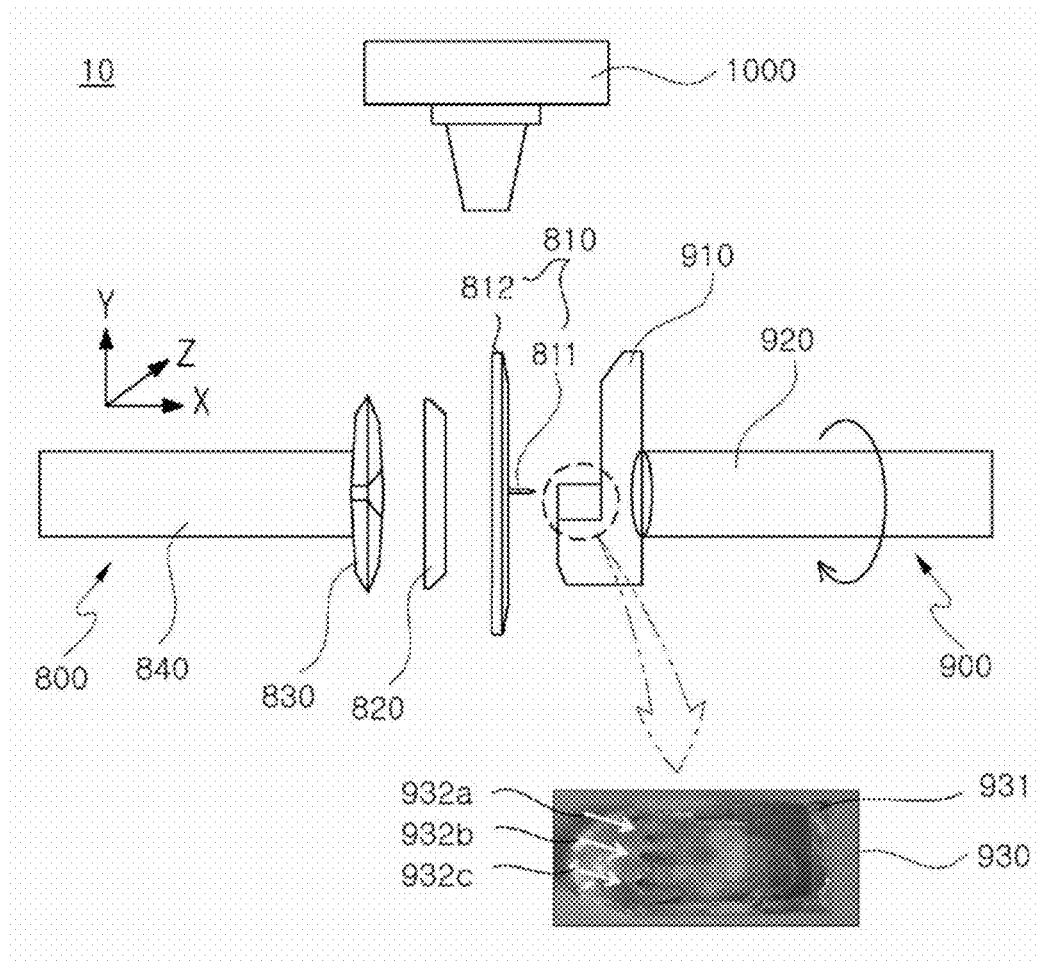
FIG. 7 is a detailed block diagram illustrating the system using the microelectrode to measure the EMG signals from the laboratory microfauna according to still another embodiment of the present disclosure.

FIG. 7 is a block diagram illustrating a process for etching away the tips of the silicon columns through the RIE according to another embodiment of the present disclosure.

Referring to FIG. 7, a silicon well 400 and an aluminum foil 500 are prepared for etching away the tips 211 and 221 of the silicon columns through the RIE. The silicon well 400 may be configured to be in a thickness of 2 nm and a depth of 1200 μm such that the silicon substrates 240, each of which being coated with the insulator, are accommodated. Silicon base parts 212 and 222 of the silicon columns 210 and 220 are accommodated within the silicon well 400 and the tips 211 and 221 thereof come out of the silicon well 400, wherein the length of the tips is set to be 100 μm.

The aluminum foil 500 is prepared for the etching away of the tips 211 and 221 of the silicon columns 210 and 220 through the RIE. The aluminum foil 500 masks the whole regions other than the tips 211 and 221, and the unmasked tips 211 and 221 of silicon columns 210 and 220 are etched away through the RIE, and a result, the coated insulators are removed. The RIE is to etch away the tips 211 and 221 of the silicon columns 210 and 220 using oxygen plasma. Thus etched away tips 211 and 221 through the RIE may be utilized for collecting the EMG signals of the microfauna.

As described above, setting the length of the tips to be 100 μm is to be properly set because of electric characteristics that under-exposed metallic layers may result in a high impedance requiring a high voltage. This avoids a situation that the fine signals of the microfauna cannot be detected because the tips 211 and 221 of the silicon columns where the metallic layers are exposed are too small. On the contrary, the over-exposed metallic layers when the tips 211 and 221 of the silicon columns are too large cause another situation that they are more sensitive to noises and may reduce options on the measurement. Hence, it is preferable to set the length of the tips 211 and 221 of the silicon columns to be neither too long nor too short, e.g., 100 μm.

Figure 8:
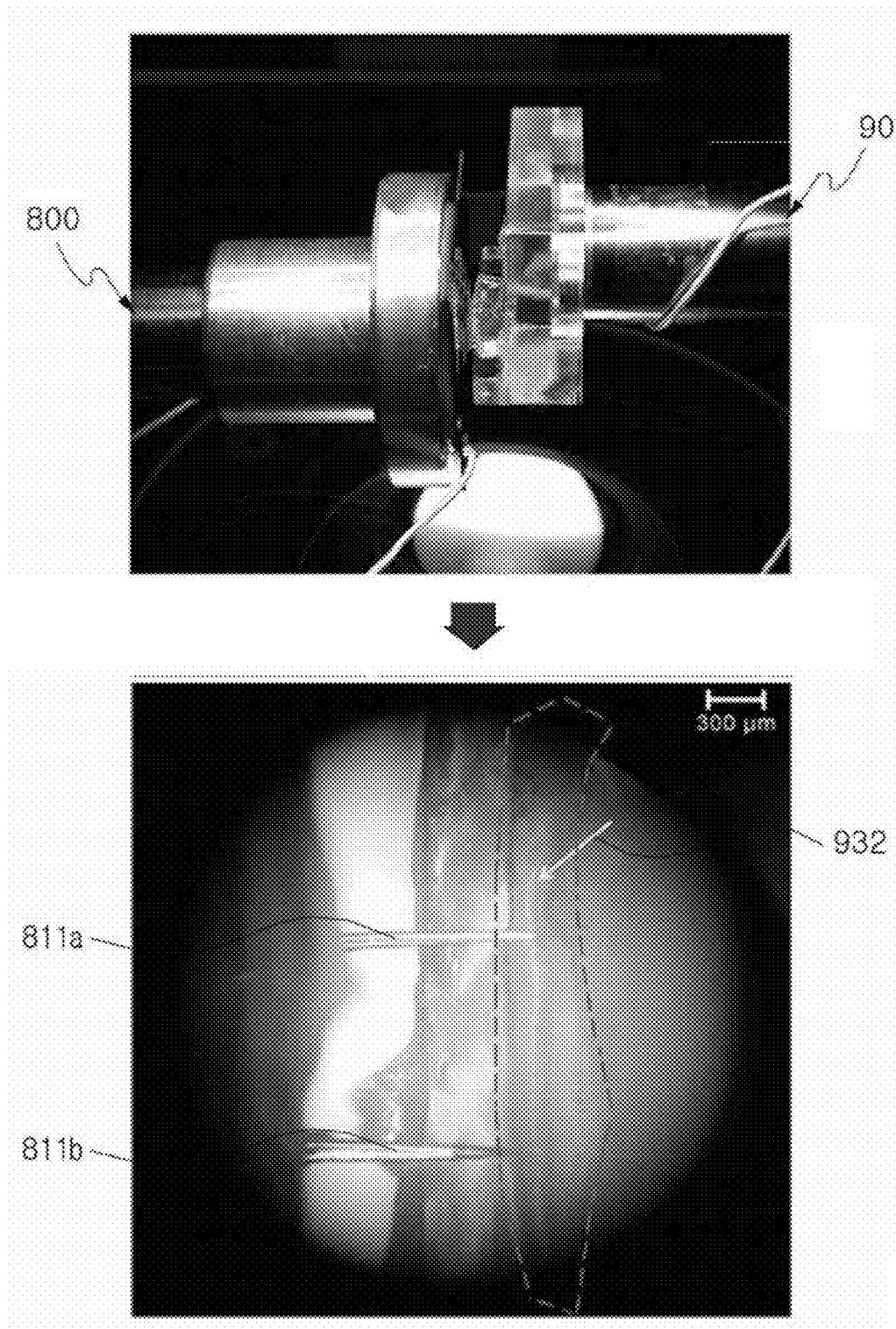
FIG. 8 is a block diagram illustrating a process of measuring the EMG signals by the system using the microelectrode to measure the EMG signals from the laboratory microfauna according to still another embodiment of the present disclosure.
Figure 9:
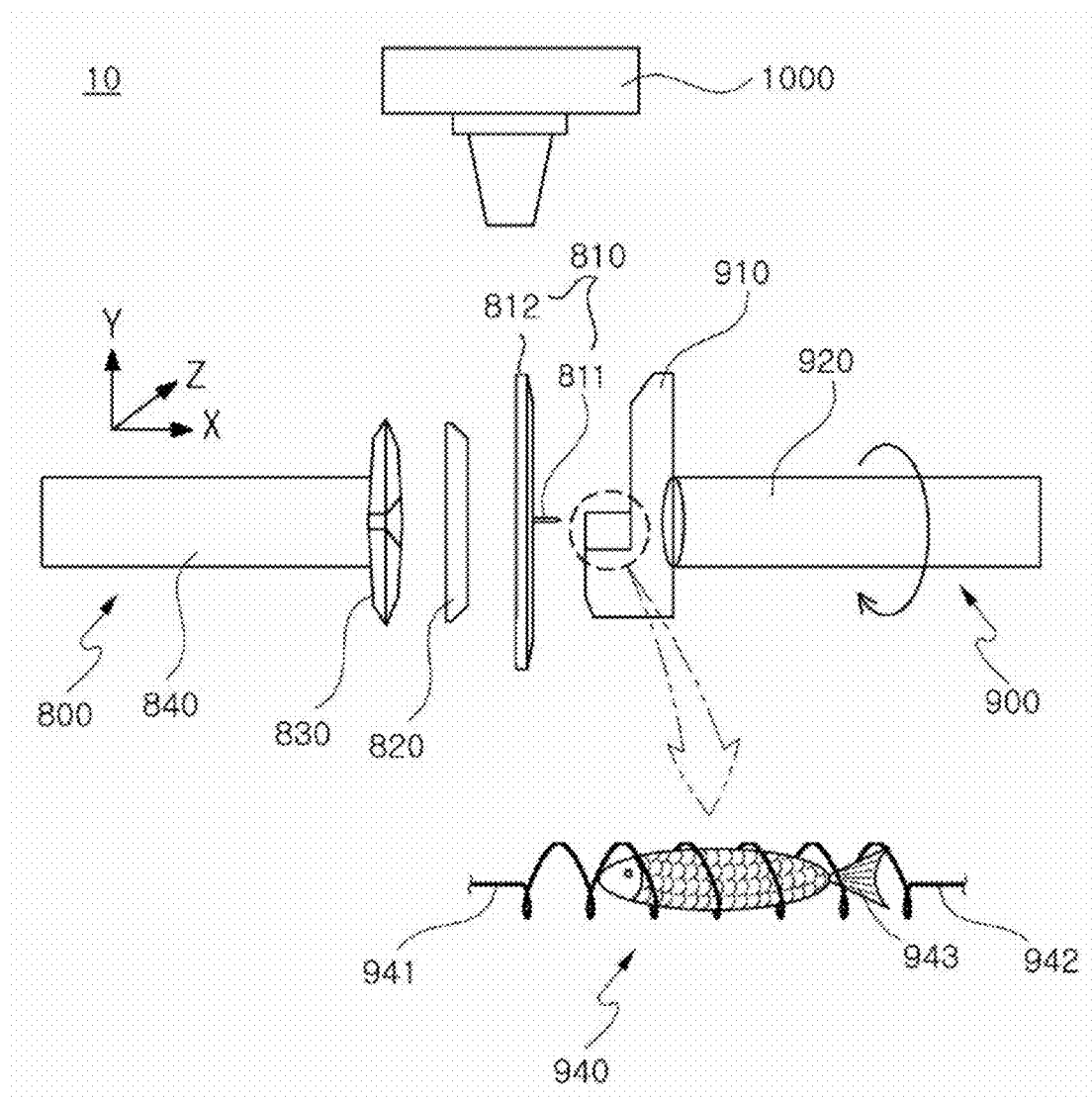
FIG. 9 is a block diagram illustrating the system using a coil electrode, which a microfauna is entwined around, to measure the EMG signals from the laboratory microfauna according to still another embodiment of the present disclosure.

FIG. 8 is a schematic block diagram illustrating a system for measuring EMG signals of laboratory microfauna using the microelectrode according to yet still another embodiment of the present disclosure, FIG. 9 is a detailed block diagram illustrating the system for measuring the EMG signals of the laboratory microfauna using the microelectrode according to still another embodiment of the present disclosure, and FIG. 10 is a block diagram illustrating a process of measuring the EMG signals through the system for measuring the EMG signals of the laboratory microfauna using the microelectrode according to still another embodiment of the present disclosure.

Referring to FIGS. 8 to 10, the system 10 for measuring the EMG signals of the laboratory microfauna using the microelectrode according to still another embodiment of the present disclosure may include a position control unit 800, a microfauna mounting unit 900 and an magnification unit 1000.

The position control unit 800 is a device for dipping a microelectrode 810 and controlling the position of the microelectrode 810 to insert the microfauna into the microelectrode 810. The microelectrode 810 used herein is one as described above with respect to the embodiments of the present disclosure. The microfauna used herein is zebrafish, and it is disposed at an opposite direction to the microelectrode 810 such that it can be inserted into the microelectrode 810 for measuring the EMG signals thereof. The position control unit 800 may move accurately on a micrometer basis in all directions and thus insert the microfauna into the microelectrode 810. The position control unit 800 may have the microelectrode 810, a rubber magnet 820, a stationary magnet 830, and a base part 840

The microelectrode 810 refers to the microelectrode manufactured through the method of the embodiments of the present disclosure and may be inserted into the microfauna and then detect the EMG signals produced from the microfauna.

The rubber magnet 820 serves to attach and fix the microelectrode 810 to one surface thereof. The rubber magnet 820 is used to minimize changes in the electrical characteristics of the microelectrode 810. The rubber magnet 820 has a predetermined thickness of, e.g., 3 mm and is coupled with the microelectrode 810 by an adhesive, e.g., epoxy. Such a rubber magnet 820 may be easily modified in its shape and thus be used for the operational convenience.

The stationary magnet 830 is a neodymium magnet which exhibits the strongest magnetism. The stationary magnet 830 is used to supplement weak magnetism of the rubber magnet 820 to firmly fix the microelectrode 810. The stationary magnet 830 is connected to the base section 840. The rubber magnet 820 and the stationary magnet 830 may be substituted with any device capable of fixing the microelectrode 810 as necessary.

The base section 840 is coupled with an external device, e.g., a device for measuring the EMG signals, to accurately adjust the position of the microelectrode 810. The base section may move in all directions. The base section 840 may deliver power supplied from an external device, to a needle electrode 811, for measuring the EMG signal from the microfauna and generate stimulation signals in association with an active electrode in the needle electrode 811 inserted into the microfauna. The microfauna produces the EMG signals in response to the stimulation signals.

The microfauna mounting unit 900 is a device to mount the microfauna for measuring the EMG signals thereon. The microfauna mounting unit 900 has a ground electrode for measuring the EMG signals. The microfauna mounting unit 900 is disposed in an opposite direction to the position control unit 800 and has a cradle section 910 and a holder section 920.

The cradle section 910 is a place where an agarose block 930 containing the microfauna is laid. The cradle section 910 has the ground electrode for measuring the EMG signals of the microfauna through the microelectrode 810. The cradle section 910 may be of a chair shape for putting thereon the agarose block 930 containing the microfauna.

The holder section 920 is coupled with the cradle section 910 to hold the microfauna. The holder section 920 may control the movement of the agarose block 930 containing the microfauna. The holder section 920 may be electrically coupled with an external device and move on a micrometer basis to rotate the agarose block 930 containing the microfauna. In addition, the holder section 920 is of a cylindrical shape but may be modified in its size and design as necessary.

The microfauna used in the present disclosure, zebrafish 932a, 932b, and 932c, are inserted into the agarose block and used for measuring EMG signals. Agarose is one of neutral polysacchride exhibiting a strong gelating tendency. The agarose may be made in a block shape by any known technique.

Using one way for making the agarose block 931, a concentrated TAE buffer solution is diluted. The diluted TAE buffer solution is mixed with agarose powders. The mixture is melted by an electronic equipment using microwaves for one minute to obtain an agarose gel. The obtained agarose gel is filled in a prepared mold of a block shape and after a given time, the agarose gel becomes cured in the block shape. The agarose block 841 is thus obtained and may be inserted into the zebrafish 932*a*, 932*b*, and 932*c* before the agarose block 931 completely solidifies. The way for inserting zebrafish 932*a*, 932*b*, and 932*c* into the agarose block 931 is not limited thereto but rather there may be a variety of ways.

Thus obtained agarose block 931 may have a dimension of, e.g., 0.7×1.5×0.3 mm An average body length of the zebrafish 932*a*, 932*b*, and 932*c* to be inserted into the agarose block 931 is 300 µm and a total volume of the zebrafish 932*a*, 932*b*, and 932*c* inserted into the agarose block 931 occupies 0.8% of the agarose block 931. The zebrafish 932*a*, 932*b*, and 932*c* to be inserted into the agarose block 931 are zebrafish embryos. Such a way to insert the zebrafish embryos for making the agarose block 931 is not limited thereto.

The magnification unit 1000 is a device for magnifying to show the microelectrode 810 and the microfauna inserted into the agarose block 930. The magnification unit 1000 magnifies to show the microelectrode 810 such that the microelectrode 810 can be exactly inserted into the microfauna. The magnification unit 1000 is a microscope and is disposed at a top of a place where the microelectrode 810 is inserted into the microfauna.

FIG. 9 is a block diagram illustrating the system for measuring the EMG signals of the microfauna using a coil electrode containing the microfauna, to according to still another embodiment of the present disclosure.

Referring to FIG. 9, the zebrafish 943, the microfauna, used in the present disclosure is not disposed in the agarose block but in the coil electrode 940, to be used for measuring the EMG signals. The coil electrode 940 may be modified according to a size of the microfauna in its size to wind around the microfauna.

For example, the coil electrode 940 is made from good conductive materials such as stainless steel. The coil electrode 940 is of a coil shape in which a wire having a diameter of 1 mm or 2 mm is wound and both ends extend lengthways by 2 cm. Thus the coil electrode 940 directly contacts with a skin surface of the microfauna and acts as a reference electrode 941 and a ground electrode 942. The coil electrode 940 having such a shape may increase a signal to noise ratio. As in a case where the coil electrode 940 consisting of the reference electrode 941 and the ground electrode 942 is employed in the system for measuring the EMG signals according to still another embodiment of the present disclosure, such a system for measuring the EMG signals may employ a microelectrode composed of a single needle electrode instead of two needle electrodes.

The method according to the present disclosure may be implemented in codes stored on a computer readable storage medium. The computer readable storage medium may encompass all types of storage devices for storing data readable by a computer system. Examples of the computer readable storage medium may include ROMs, RAMs, CD-ROMs, magnetic tapes, floppy disks, optical data storage devices and so on as well as something implemented in a form of carrier waves (e.g., transport via Internet). Further, the computer readable storage medium may be distributed over multiple computer systems interconnected via a network, such that the computer readable codes can be stored and executed on the computer systems.

Although the present disclosure has been described with reference to the aforementioned embodiments illustrated in the drawings, it is to be understood that they are merely exemplary and it is possible for those skilled in the art to alter, change, or modify these examples.

Therefore, the technical scope of the present disclosure should be defined by the appended claims.

What is claimed is:

1. A system for measuring bio-signals from laboratory microfauna using a microelectrode, comprising:
   a position control unit, attached to the microelectrode, for controlling a position of the microelectrode;
   a microfauna mounting unit for mounting the laboratory microfauna, disposed at an opposite direction to the position control unit, for dipping the laboratory microfauna; and
   a magnification unit for magnifying the microelectrode and the laboratory microfauna in order to control the position control unit and the microfauna mounting unit, contact the microelectrode to the laboratory microfauna, and measure the bio-signals from the laboratory microfauna,
   wherein the microfauna mounting unit has a coil electrode having a shape for winding around the laboratory microfauna.

2. The system of claim 1, wherein the position control unit includes a magnet section disposed at one side of the microelectrode to fix the microelectrode.

3. The system of claim 1, wherein the position control unit supplies an electric power generated from an external device to a plurality of needle electrodes included in the microelectrode, such that the plurality of needle electrodes may deliver stimulus signals to the laboratory microfauna, thereby measuring the bio-signals from the laboratory microfauna.

4. The system of claim 1, wherein the coil electrode has a diameter of 1 mm or 2 mm.

5. The system of claim 1, wherein the microfauna mounting unit may be rotated such that the microelectrode may be accurately inserted into the laboratory microfauna.

6. The system of claim 1, wherein the coil electrode is composed of an electric conductive material and both ends of the coil electrode are grounded.

* * * * *